United States Patent
Tseng (10) Patent No.: US 6,939,306 B2
(45) Date of Patent: Sep. 6, 2005

(54) METHOD FOR MEASURING BLOOD PRESSURE AND PULSE RATE WITH A PUMP-LESS MECHANICAL COMPRESSION APPARATUS

(75) Inventor: Daniel C. M. Tseng, Taipei Hsien (TW)

(73) Assignee: K-Jump Health Co., Ltd., Taipei Hsien (TW)

( * ) Notice: Subject to any disclaimer, the term of this patent is extended or adjusted under 35 U.S.C. 154(b) by 175 days.

(21) Appl. No.: 10/652,076

(22) Filed: Sep. 2, 2003

(65) Prior Publication Data

US 2005/0049512 A1 Mar. 3, 2005

(51) Int. Cl.[7] .................................................. A61B 5/02
(52) U.S. Cl. ........................ 600/494; 600/499; 600/490
(58) Field of Search ................................. 600/490–499, 600/500–503

(56) References Cited

U.S. PATENT DOCUMENTS

| | | | |
|---|---|---|---|
| 5,176,143 A | * | 1/1993 | Eckerle et al. .............. 600/490 |
| 6,027,452 A | * | 2/2000 | Flaherty et al. ............. 600/485 |
| 6,632,181 B2 | * | 10/2003 | Flaherty et al. ............. 600/485 |

* cited by examiner

Primary Examiner—Robert Wagard
Assistant Examiner—Navin Natnithithadha
(74) Attorney, Agent, or Firm—Birch, Stewart, Kolasch & Birch, LLP (57) ABSTRACT

A method for measuring blood pressure and pulse rate with a pump-less mechanical compression apparatus, wherein the pump-less mechanical compression apparatus comprises a compression assembly with a closed system air bag having a fixed air volume fastened on the human body measuring site; a sensor coupled to the air bag for sensing pressure change inside the air bag; a processor for processing the pressure change; and a display. Through the use of the mechanical compression assembly, the pressure inside the air bag can be increased and steadily released to achieve the same measuring effects as traditional sphygmomanometer/ sphygmometer. The apparatus invention also comprises a deactivation assembly and an alarm for safety purpose.

5 Claims, 7 Drawing Sheets

METHOD FOR MEASURING BLOOD PRESSURE AND PULSE RATE WITH A PUMP-LESS MECHANICAL COMPRESSION APPARATUS

FILED OF THE INVENTION

The present invention relates to sphygmomanometers and sphygmometers and more particularly to a method for measuring blood pressure and pulse rate with a pump-less mechanical compression apparatus.

BACKGROUND OF THE INVENTION

As defined, blood pressure is the pressure exerted by the blood against the inner walls of the blood vessel, especially the arteries. Also, heart can receive blood from the veins and pump it through the arteries by alternate dilation and contraction. As such, pressure can be expressed as either contraction pressure (i.e., pressure exerted by the blood pumped from the heart against the inner walls of the arteries) or dilation pressure (i.e., exerted by the blood against the inner walls of the arteries when the heart stops contracting in a predetermined short period of time). Pulse rate can also be measured by a typical electronic sphygmometer. As defined, pulse is the regular beating in the arteries caused by the contraction and the dilation of the heart.

A typical electronic sphygmomanometer is advantageous for being compact, having a digital display, and without the cooperation of a stethoscope. Thus, the typical electronic sphygmomanometers are gaining popularity among consumers. The typical electronic sphygmomanometer is characterized in that an air bag is inflated by a pump, then pressure of the air bag is slowly released by a pressure release device, a sensor is deformed due to the pressure change inside the air bag, the differential electrical resistance of the sensor is then measured by the Wheatstone bridge, and finally a blood pressure is displayed.

Figure 1:
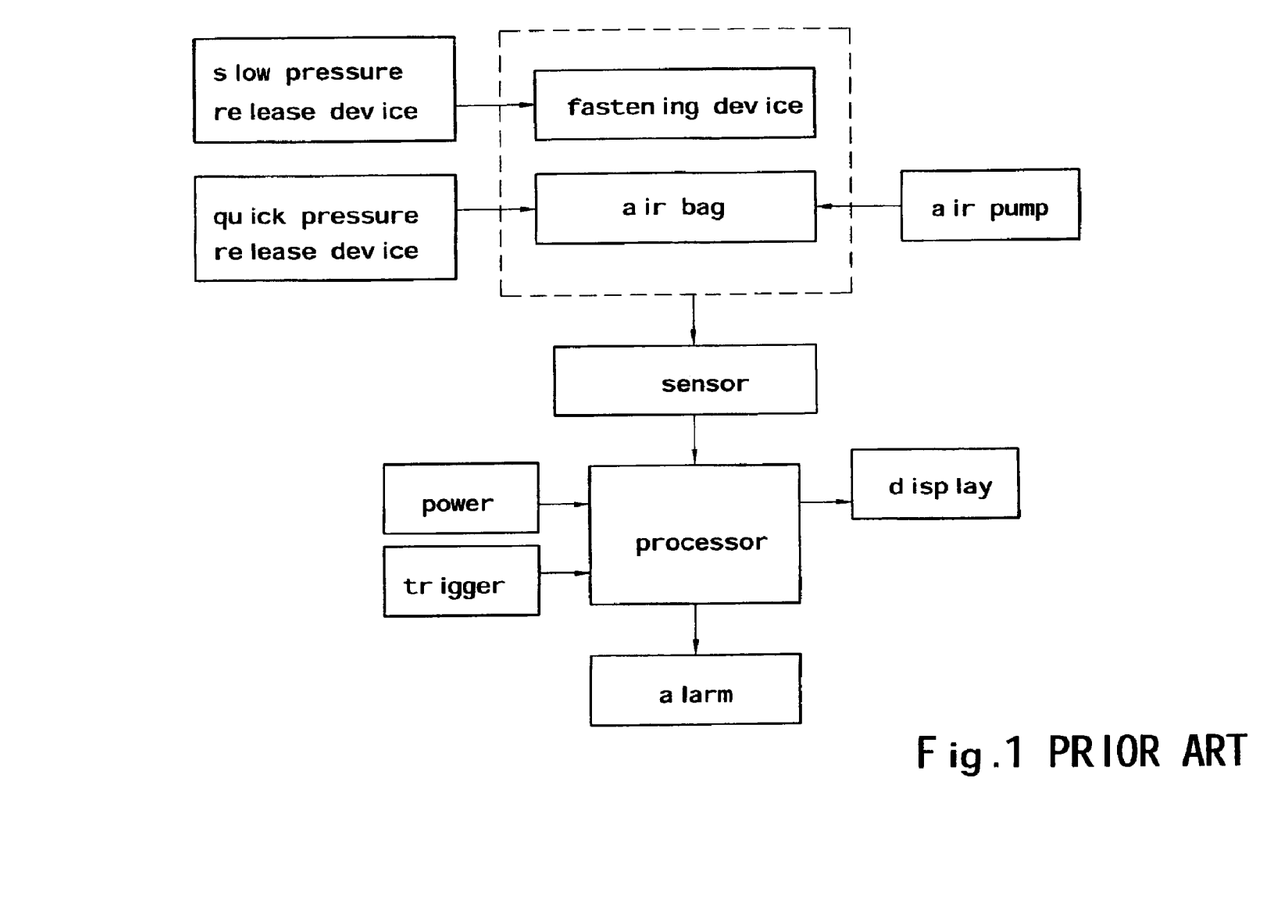
FIG. 1 is a block diagram of a conventional electronic sphygmomanometer.

Referring to FIG. 1, there is shown a block diagram of the typical electronic sphygmomanometer. The sphygmomanometer comprises a processor, an air pump controlled by the processor for pumping air into an air bag until a predetermined pressure is reached, a slow pressure release device is adapted to release pressure of the air bag, and other associated devices (e.g., power, alarm, display, sensor, trigger, fastening device, and quick pressure release device). However, the prior art suffers from several disadvantages. For example, for the sake of portability and the trend of compactness, the bulky pump and pressure release devices are not desirable. Further, strong noise is generated by the pump and the pressure release devices in operation. Hence, a need for improvement exists.

SUMMARY OF THE INVENTION

It is an object of the present invention to provide a method for measuring blood pressure and pulse rate by activating a pump-less mechanical compression apparatus, comprising the steps of fastening the unit with an air bag, which is a closed system containing fixed air volume, on the human body measuring site; activating the mechanical compression assembly to exert pressure on the air bag towards the human body and thus increase the pressure inside the air bag; release the mechanical compression on the air bag for the air bag pressure to steadily return to its original state and allow the sensor to measure the pressure change for calculating values; sending the values to the processor; processing the values by the processor to obtain a blood pressure including a contraction pressure and a dilation pressure, and a pulse rate; and showing the contraction pressure, the dilation pressure, and the pulse rate on a display.

It is another object of the present invention to provide a pump-less mechanical compression apparatus applied on a sphygmomanometer/sphygmometer, comprising a closed system air bag containing fixed air volume fastened on the human body; a sensor coupled to the air bag for sensing pressure change inside the air bag; a processor for processing the pressure change; a display for showing the measured contraction pressure, dilation pressure, and pulse rate; and a compression assembly, whereby activating the mechanical compression assembly to exert pressure on the air bag towards the human body measuring site will cause the pressure inside the air bag to increase and when the compression assembly is deactivated, the pressure will decrease and the change will be transmitted to the sensor and the processor for processing sequentially in order to calculate a contraction pressure, a dilation pressure, and a pulse rate, and show the contraction pressure, the dilation pressure, and the pulse rate on the display.

The above and other objects, features and advantages of the present invention will become apparent from the following detailed description taken with the accompanying drawings.

DETAILED DESCRIPTION OF THE PREFERRED EMBODIMENTS

Figure 5:
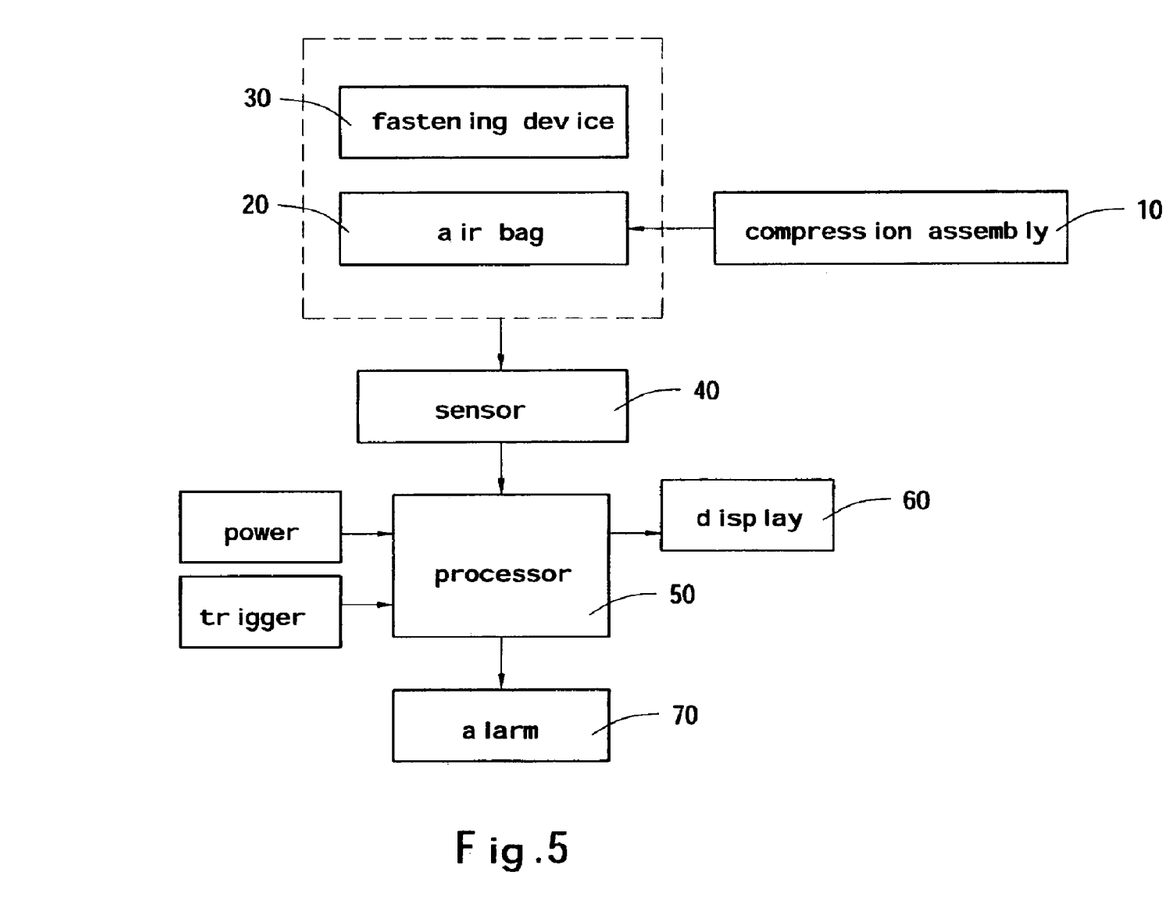
FIG. 5 is a block diagram of the pump-less mechanical compression sphygmomanometer/sphygmometer of the invention.

Referring to FIG. 5, the pump-less mechanical compression apparatus applied on a sphygmomanometer/sphygmometer comprises a fastening device 30 having an air bag 20, which is a closed system with fixed air volume, fastened at the measuring site (e.g., the wrist) of the body, a sensor 40 coupled to the air bag 20 for sensing pressure change inside the air bag 20, a processor 50 for processing the pressure change, a display 60 for showing the measured results of contraction pressure, dilation pressure, and pulses in a digital form, and a compression assembly 10. During compression, the compression assembly 10 is adapted to gradually exert pressure on the air bag 20 towards the measuring site such as the wrist. The pressure is increased inside the air bag and the pressure change is detected by the sensor 40. During decompression, the compression assembly 10 is adapted to gradually return to its original state and thus the pressure on the air bag 20 is decreased. The pressure change inside the air bag 20 is detected by the sensor 40. This forms a small, pump-less, mechanical compression sphygmomanometer/sphygmometer of the invention.

Figure 2A:
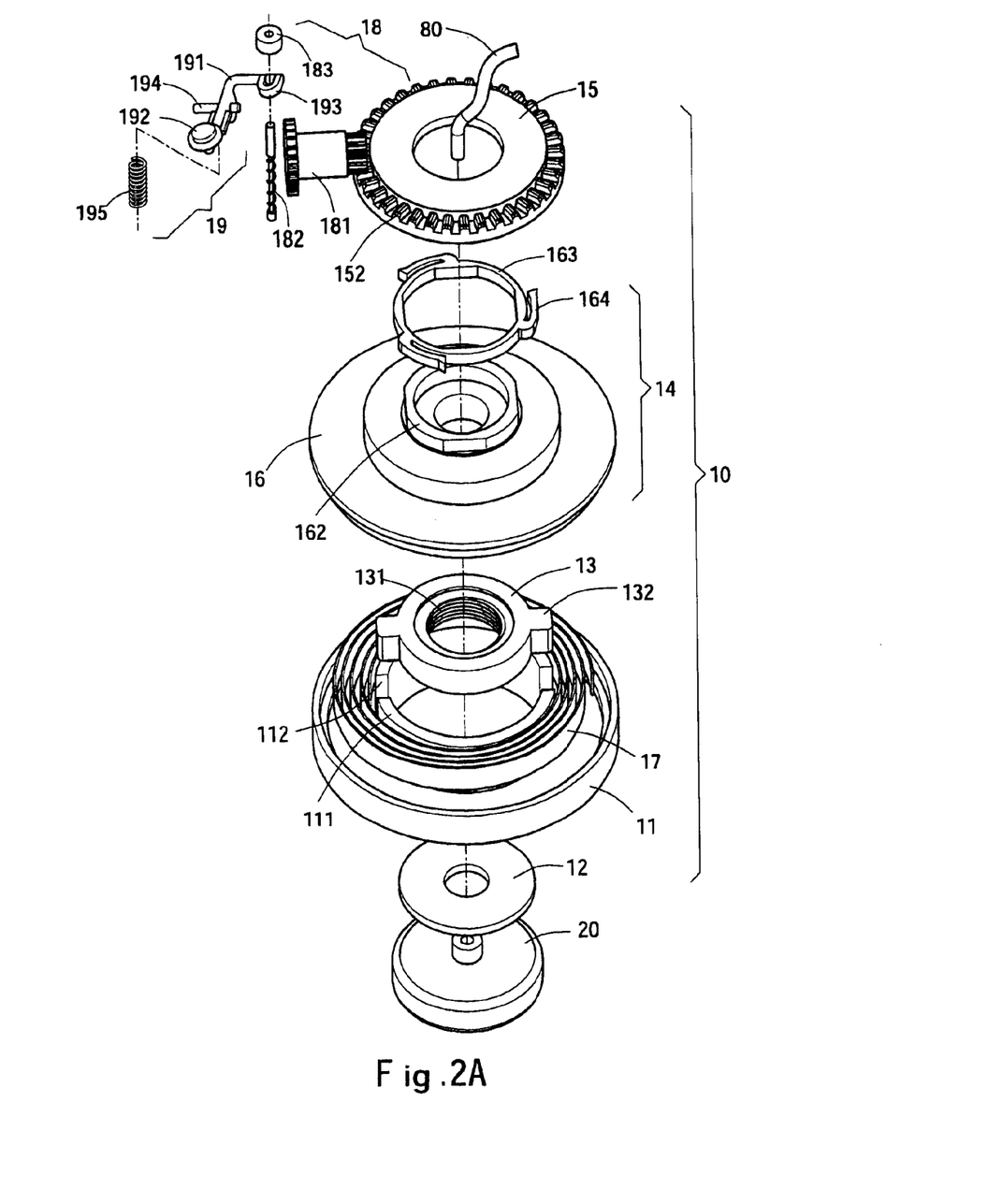
FIGS. 2A and 2B are exploded views of a pump-less mechanical compression sphygmomanometer/sphygmometer according to the invention.
Figure 2B:
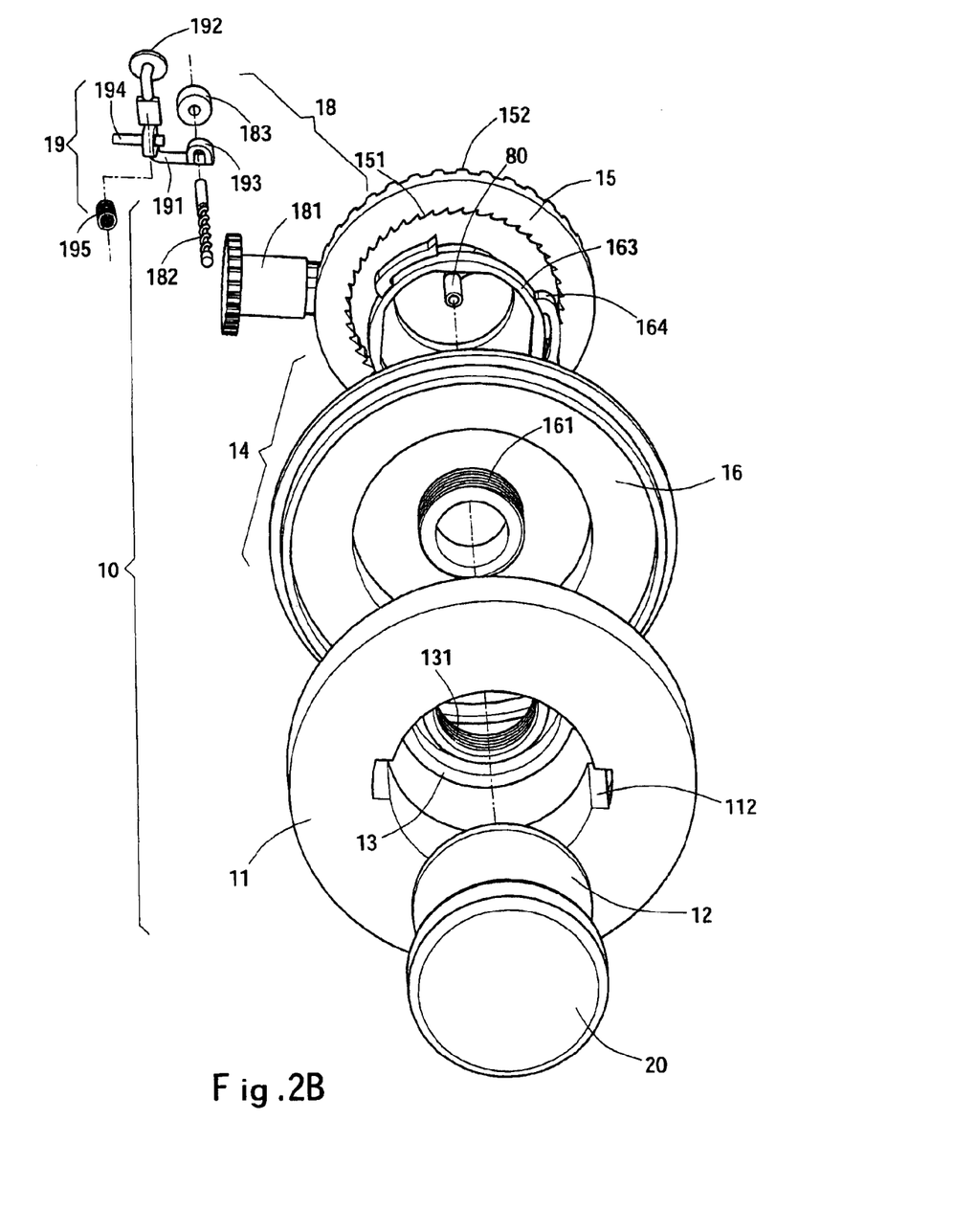

Referring to FIGS. 2A and 2B, components of the inventions will be described in detail below. The compression assembly 10 comprises a holed, annular seat 11 including a lower, central cavity for receiving the air bag 20, two opposite, upper arc walls 111 around a hole thereof, and two opposite slots 112, an abutment disk 12 on top of the air bag 20, a sleeve-like moveable member 13 on the abutment disk 12, the moveable member 13 being moveable within a predetermined distance to and fro in the hole of the seat 11, the moveable member 13 having internal threads 131 and two opposite projections 132 on its outer surface, the projections 132 being slidably fitted in the slots 112, a force exertion assembly 14 for exerting a turning force on the moveable member 13 or stopping exerting force thereon, the force exertion assembly 14 including an annular, holed turning member 16 including a central, externally threaded extension 161 on the underside, the externally threaded extension 161 being coupled to the internal threads 131, an annular flange 162 around a hole of the turning member 16, and a ring 163 put on the flange 162, the ring 163 having three spaced external hooks 164, a gear 15 including a ratchet section 151 on its underside for catching and holding the hooks 164, and an annular, toothed section 152 on its top, a speed regulator 18 including a shaft 181 having threads coupled to the toothed section 152, a cylinder 182 having external threads coupled to the shaft 181, and a weight 183 provided on the cylinder 182, and a mainspring 17 anchored around the arc walls 111, and a deactivation assembly 19 including a lever element 191 having a pivot 194, a connecting element 193 at one end coupled to the cylinder 182, a trigger element 192 at the other end, and a spring 195.

Figure 3A:
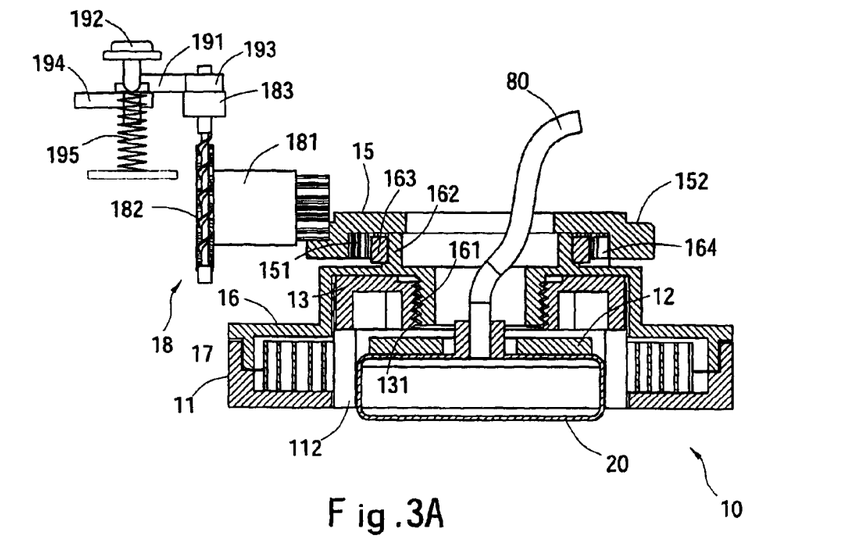
FIGS. 3A and 3B are cross-sectional views of the pump-less mechanical compression sphygmomanometer/sphygmometer of the invention for illustrating the expanded and the contracted states of the closed system air bag respectively.
Figure 3B:
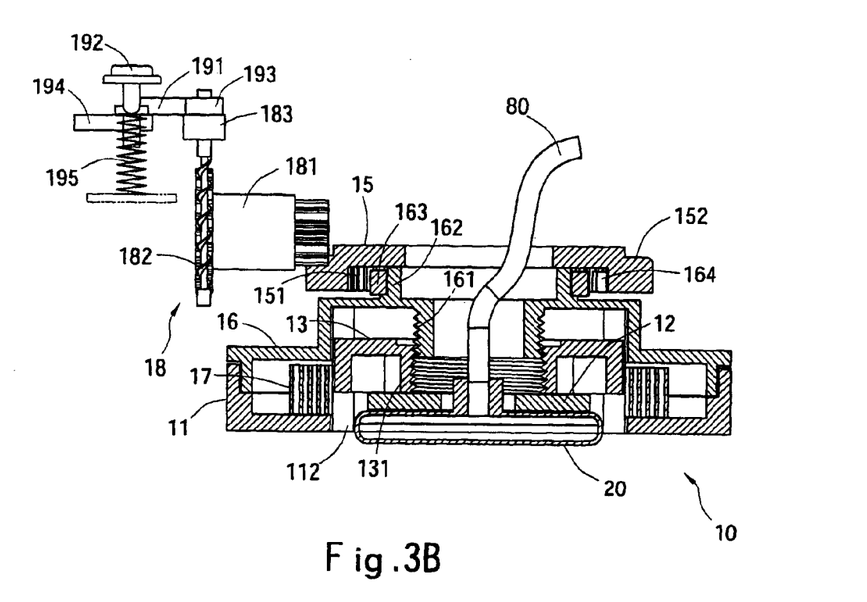
Figure 6:
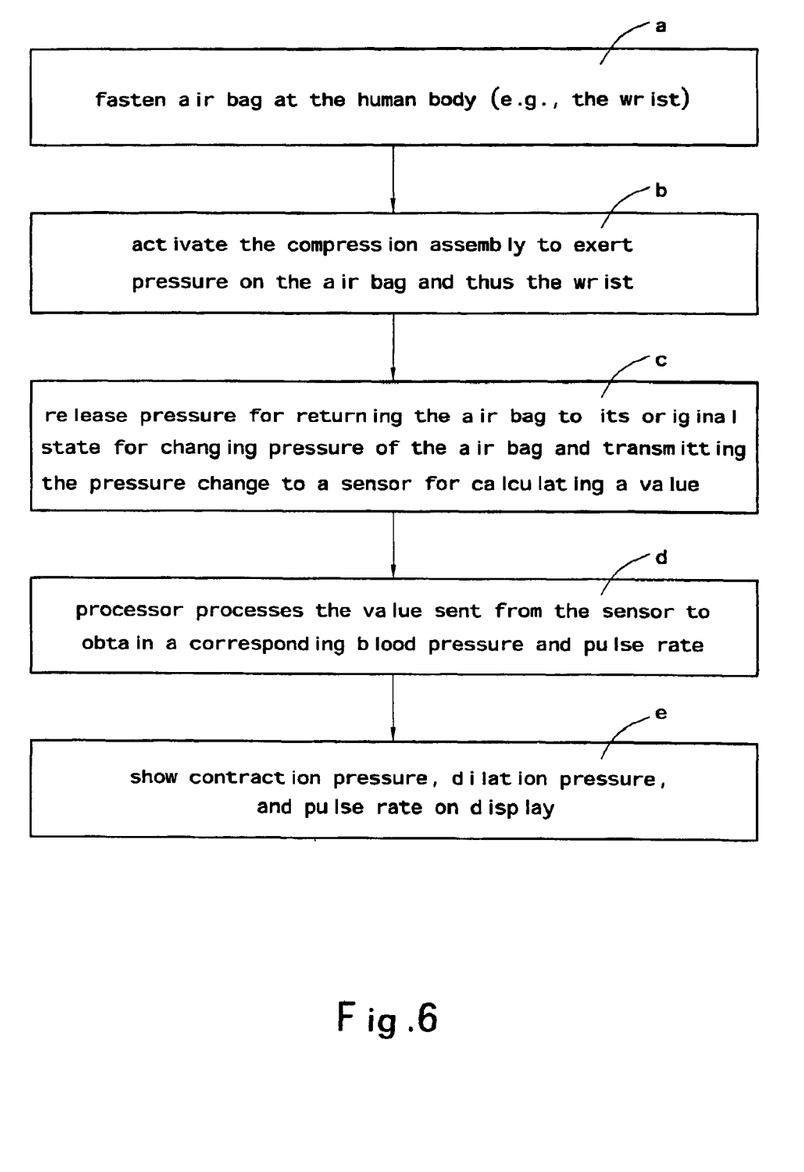
FIG. 6 is a flow chart illustrating a process according to the invention.

Referring to FIG. 6 in conjunction with FIGS. 3A, 3B, and 5, a process of the invention comprises the following steps:

Step a: Fasten the air bag 20 at the measuring site (e.g., the wrist) of the body by wrapping the fastening device therearound.

Step b: Activate the compression assembly 10 to gradually exert pressure on the air bag 20 and onto the wrist. At the same time, the sensor 40 senses the pressure change inside the air bag 20. In the pressure exertion process, the turning member 16 rotates a number of times. Further, the internal threads 131 move downward due to threaded connection to the externally threaded extension 161. The abutment disk 12 then moves downward in response to the downward movement of the moveable member 13. Next, the air bag 20 contracts to press on the wrist in response to the downward movement of the abutment disk 12. The pressure change inside the air bag 20 is transmitted to the sensor 40 through the duct 80 which is coupled to and connected between the air bag 20 and the sensor 40. Also, the mainspring 17, being connected to the arc walls 111 and annular seat 11, is coiled during the pressure exertion process for storing elastic energy. Further, the gear 15 is motionless in the pressure exertion process because the rotating direction of hooks 164 does not positively engage the ratchet section 151.

Step c: Release pressure of the compression assembly 10 for returning the air bag 20 to its original state in which the pressure change inside the air bag 20 is transmitted to the sensor 40 for calculating a value.

Step d: The value is sent from the sensor 40 to the processor 50 for processing in order to obtain a corresponding blood pressure including a contraction pressure and a dilation pressure, and a pulse rate. Note that all of the contraction pressure and dilation pressure, and the pulse rate are measured during the decompression (deflating) process of the air bag 20. In detail, the stored elastic force of the mainspring 17 is released gradually by uncoiling for facilitating the upward movement of the moveable member 13. Moveable member 13 moves upward while the expanding air bag 20 urges against the abutment disk 12. Further, the turning member 16 rotates in a direction opposite to that in pressure exertion process due to the upward movement of the moveable member 13. The ring 163 and ratchet section 151 are positively engaged and thus the gear 15 is free to rotate. The speed regulator 18 aims at providing a constant rotation mode in which the cylinder 182 is adapted to provide a constant rotating speed, the relative rotating speed of the shaft 181 about the gear 15 is determined by the cylinder 182 with the gear 15, the turning member 16, the moveable member 13, and the abutment disk 12 being moved upward, and the weight 183 is adapted to provide a steady upward movement of the same. This facilitates the obtaining of a more precise blood pressure and the pulse rate.

Step e: Contraction pressure, dilation pressure, and pulse rate are transmitted from the processor 50 to the display 60 for showing in a digital form. The invention further comprises an alarm 70 coupled to the processor 50. The alarm 70 will issue a warning when output pressure of the compression assembly 10, as sensed by the sensor 40, reaches a limit value.

Figure 4A:
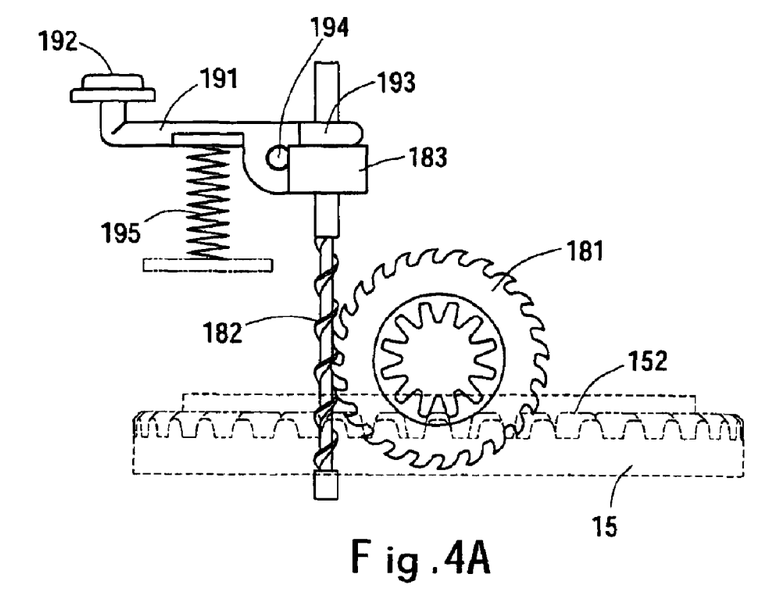
FIGS. 4A and 4B are side elevational views for illustrating the process of changing from the operating state to the disabled state of the deactivation assembly.
Figure 4B:
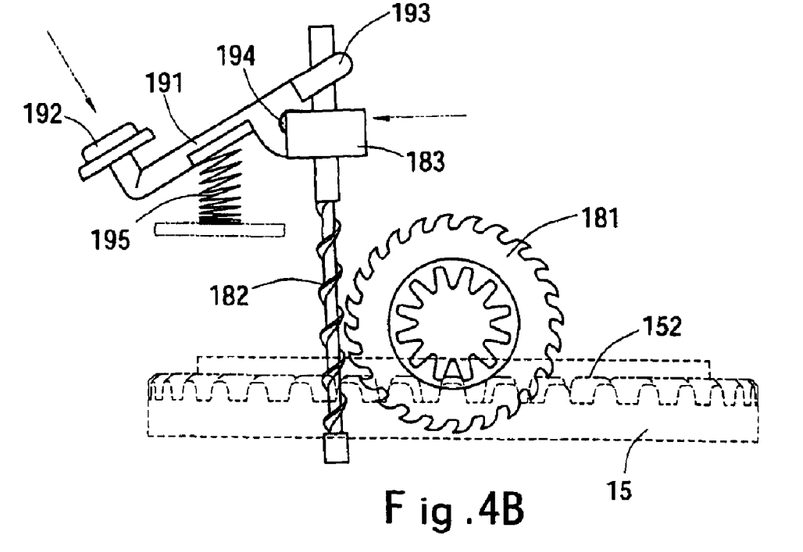

It is possible that a person may feel uncomfortable during the blood pressure measuring process while pressure exerted on his/her wrist by the air bag 20 is increasing. In this case the person or the medical worker has to activate the deactivation assembly 19 to disable the pump-less mechanical compression apparatus applied in sphygmomanometer/sphygmometer via the speed regulator 18. Referring to FIGS. 4A and 4B, the operation of the deactivation assembly 19 is described below. In response to exerting force on the trigger element 192 of the lever element 191, the lever element 191 moves downward for compressing the spring 195 for storing elastic force therein. Next, the lever element 191 pivots about the pivot 194 for causing the connecting element 193 to lift and the cylinder 182 is thus slanted by the connecting element 193. Next, the slanted cylinder 182 disengages from the shaft 181. As such, rotation of the toothed section 152 of the gear 15 is not stopped by the shaft 181. As a result, the compressed states of the air bag 20 and thus the wrist of the person are changed to the uncompressed states by the release of the stored elastic force of the mainspring 17 if a person feels uncomfortable during the blood pressure measuring process. Once being uncompressed, the stored elastic force of the spring 195 below the trigger element 192 is released immediately to cause all components of the deactivation assembly 19 to return to their original states.

It will be evident from the foregoing that the invention has the following advantages: No provision of the bulky pump and pressure release device, resulting in compactness. Also, minimal noise is generated while measuring blood pressure and pulse rate. Moreover, the speed regulator 18 can provide a stable and steady decompression rate for pressure release and thus help facilitate the obtaining of a more precise blood pressure and the pulse rate.

While the invention herein disclosed has been described by means of specific embodiments, numerous modifications and variations could be made thereto by those skilled in the art without departing from the scope and spirit of the invention set forth in the claims.

What is claimed is:

1. A pump-less mechanical compression apparatus, comprising:
　　a closed system air bag with fixed air volume fastened at the human body;
　　a sensor coupled to the air bag for sensing pressure change inside the air bag;
　　a processor for processing the pressure change;
　　a display for showing the measured contraction pressure, dilation pressure, and pulse rate; and
　　a compression assembly;
　　whereby activating the compression assembly to exert pressure on the closed system air bag and the human body will cause a pressure change inside the air bag and, meanwhile the pressure changes are transmitted to the sensor and the processor for processing sequentially when the compression assembly is deactivated so as to calculate a contraction pressure, a dilation pressure, and a pulse rate, and show the contraction pressure, the dilation pressure, and the pulse rate on the display.

2. The pump-less mechanical compression apparatus of claim 1, wherein the compression assembly comprises:
　　a holed, annular seat including a lower and a central cavity for receiving the air bag, two opposite, upper arc walls around a hole of the seat, and two opposite slots, an abutment disk on top of the air bag, and a sleeve-like moveable member on the abutment disk, the moveable member being moveable within a predetermined distance to and fro in the hole of the seat, the moveable member having internal threads and two opposite projections on its outer surface, the projections being slidably fitted in the slots;
　　a force exertion assembly for exerting force on the moveable member or stopping exerting force thereon, the force exertion assembly including an annular, holed turning member including a central, a externally threaded extension in an underside, wherein the externally threaded extension being threaded coupled to the internal threads, an annular flange around the hole of the turning member, and a ring put on the flange, the ring having a plurality of spaced external hooks;
　　a gear including a ratchet section on an underside for catching and holding the hooks, and an annular, a toothed section on a top;
　　a speed regulator including a shaft having threads coupled to the toothed section, a cylinder having external threads coupled to the shaft, and a weight on the cylinder; and
　　a mainspring around the arc walls, and further comprising a duct coupled to and being in communication between the air bag and the sensor,
　　whereby exerting pressure on the air bag will turn the turning member with a predetermined times, move the internal threads and the moveable member downward, move the abutment disk downward, contract the air bag to press on the human body, transmit the pressure change inside the air bag to the sensor via the duct, coil the mainspring, and maintain the gear to be motionless; or stopping exerting pressure on the air bag will uncoil the mainspring, allow the air bag to expand against the abutment disk to move the moveable member upward, rotate the turning member in a direction opposite to that in the pressure exertion, and rotate the ring and the gear.

3. The pump-less mechanical compression apparatus of claim 2, further comprising a deactivation assembly including a lever element having a pivot, a connecting element at one end coupled to the cylinder, a trigger element at the other end, and resilient means wherein responsive to exerting force on the trigger element, the pivot element moves downward for compressing the resilient means, the lever element pivots about the pivot for causing the connecting element to lift and the cylinder to slant for disengaging quickly from the shaft, a rotation of the toothed section is unrestricted, the compressed air bag is changed quickly to an uncompressed state, and the resilient means is expanded to cause the deactivation assembly to return to its original state.

4. A method for measuring blood pressure and pulse rate with a pump-less mechanical compression apparatus, comprising the steps of:
　　fastening an air bag, which is a closed system with fixed air volume, on the human body;
　　activating a compression assembly to exert pressure on the closed system air bag and onto the human body;
　　releasing pressure for returning the air bag to its original state for causing a pressure change inside the air bag and transmitting the pressure change to a sensor for calculating a value;
　　sending the value to a processor for processing in order to obtain a blood pressure including a contraction pressure and a dilation pressure, and a pulse rate; and
　　showing the contraction pressure, the dilation pressure, and the pulse rate on a display.

5. The method of claim 4, further comprising an alarm coupled to the processor, the alarm being adapted to issue a warning when the output pressure of the compression assembly, as sensed by the sensor, reaches a limit value.

* * * * *